(12) United States Patent
Visconti

(10) Patent No.: US 11,096,777 B2
(45) Date of Patent: Aug. 24, 2021

(54) BREAST SHAPING METHOD USING BARBED SUTURE AND SUTURE HANDLING DEVICE IN BREAST FAT GRAFTING

(71) Applicants: WOW MEDICAL INC., Seoul (KR); Bumsoo Kim, Seoul (KR)

(72) Inventor: Giuseppe Visconti, Rome (IT)

(73) Assignees: WOW MEDICAL INC.; Bumsoo Kim

( * ) Notice: Subject to any disclaimer, the term of this patent is extended or adjusted under 35 U.S.C. 154(b) by 163 days.

(21) Appl. No.: 16/284,755

(22) Filed: Feb. 25, 2019

(65) Prior Publication Data
US 2020/0155302 A1    May 21, 2020

(30) Foreign Application Priority Data

Nov. 21, 2018   (KR) ........................ 10-2018-0144744

(51) Int. Cl.
*A61F 2/12*   (2006.01)
*A61B 17/06*   (2006.01)
*A61B 17/00*   (2006.01)

(52) U.S. Cl.
CPC .......... *A61F 2/12* (2013.01); *A61B 17/06166* (2013.01); *A61B 2017/00792* (2013.01); *A61B 2017/00796* (2013.01); *A61B 2017/00884* (2013.01); *A61B 2017/00969* (2013.01); *A61B 2017/06176* (2013.01); *A61L 2430/04* (2013.01); *A61L 2430/34* (2013.01); *A61M 2202/08* (2013.01)

(58) Field of Classification Search
CPC .. A61F 2/12; A61F 2/0059; A61F 2/52; A61L 2430/04; A61L 2430/34; A61B 2017/06176; A61B 2017/0496; A61B 2017/00792; A61B 2017/00796; A61B 5/6883; A61B 17/06166
See application file for complete search history.

(56) References Cited

U.S. PATENT DOCUMENTS

| 7,871,425 | B2 * | 1/2011 | Jones | ............... A61B 17/06166 |
| | | | | 606/224 |
| 2008/0082129 | A1 * | 4/2008 | Jones | ........................ A61F 2/12 |
| | | | | 606/232 |
| 2009/0248071 | A1 * | 10/2009 | Saint | ................... A61B 17/0401 |
| | | | | 606/232 |
| 2015/0032140 | A1 * | 1/2015 | Khouri | ............... A61B 17/0482 |
| | | | | 606/172 |

* cited by examiner

*Primary Examiner* — Jennifer Dieterle
*Assistant Examiner* — Amanda M Barkan
(74) *Attorney, Agent, or Firm* — Mendelsohn Dunleavy, P.C.

(57) ABSTRACT

A breast shaping method using a barbed suture and a suture handling device. The breast shaping method includes inserting a tensioning barbed suture in medialmost and lateralmost portion of the inframammary fold from deep soft tissues (muscle/pericondrium-periostium to and along the subdermal layer of the inframammary fold, with an end portion of the barbed suture being left outside of the skin, thereby allowing the barbed suture to be tensioned, tensioning the end portion of the barbed suture arranged by the insertion of the barbed suture, so that the barbed suture pulls tissues of the subdermal layer, thereby lifting the inframammary fold and defining a nice indentation of the inframammary fold, and cutting the end portion of the barbed suture outside of the skin after the tensioning of the barbed suture.

4 Claims, 8 Drawing Sheets

BREAST SHAPING METHOD USING BARBED SUTURE AND SUTURE HANDLING DEVICE IN BREAST FAT GRAFTING

CROSS REFERENCE TO RELATED APPLICATION

The present application claims priority to Korean Patent Application No. 10-2018-0144744, filed Nov. 21, 2018, the entire contents of which is incorporated herein for all purposes by this reference.

BACKGROUND OF THE INVENTION

Field of the Invention

The present invention relates generally to breast shaping for women and, more particularly, to a breast shaping method using a barbed suture and a suture handling device in breast, especially after breast fat grafting, by which a the boundary lines of a breast as well as the lower pole convexity can be more clearly defined also thanks to the edema control and favorable redirection which further enhance lower pole convexity in the postoperative healing time exerted by the positioned threads, so that the breast can be shaped to be more aesthetically pleasant and natural looking as well as it allows to correct breast malformations and asymmetry.

Description of the Related Art

Not only having a beautiful face, but also a slim, busty and harmonic body, may be common interests among women. In particular, the breasts having an attractive volume or shape are regarded as typical body parts representing femininity. Women having a sexy and attractive breast shape may be envied. Moreover, breast malformations (i.e. tuberous breast, Poland syndrome etc) and breast asymmetry represents a serious physical and physiological distress for affected women.

Since there is high interest in the shape or size of breasts, women who have, for example, small, sagging, malformated or asymmetrical breasts may have strong psychological discomfort about their breasts. In this regard, some of women having psychological discomfort due to the shape or size of their breasts may attempt to shape their breasts by surgery.

Breast surgeries may include augmentation or reduction of the size of breasts, improvement of the overall appearance of breasts, and the like. Most breast augmentation surgeries are designed to increase the volumes of the breasts by implanting prostheses made of a silicone material into the breasts. Such surgical procedure includes open surgical dissection through different possible accesses (i.e. inframammary folds, periareoalar, axillary or umbilical) of an appropriate pocket (subglandular, subfascial or submuscolar) in which the breast prostheses is placed, usually conducted under general anesthesia.

However, the prosthesis implantation breast surgery can have short and long-term drawbacks, such as capsular contracture, implant malposition, implant migration, implant rupture and breast tissue sagging on implant over time. Moreover, implant placement will leave a scar.

The information disclosed in the Background of the Invention section is only for the enhancement of understanding of the background of the invention, and should not be taken as an acknowledgment or as any form of suggestion that this information forms a prior art that would already be known to a person skilled in the art.

DOCUMENTS OF RELATED ART

Korean Patent No. 10-1668997 (Dissector for Breast Augmentation Surgery)
Korean Registered Utility Model No. 20-0481188 (Endoscopic Retractor for Breast Shaping)

SUMMARY OF THE INVENTION

Accordingly, the present invention has been made keeping in mind the above problems occurring in the related art, and the present invention proposes a breast shaping method using barbed sutures, by which a breast shape having a clear contour while being high and elastic can be provided, the drawbacks of implant surgery are avoided, millimetric thus invisible scars are left, and a recovery time can be significantly reduced due to absence of skin dissection, and more particularly, the effect of the surgery is immediate.

It is also provided a barbed suture handling device that can tension and cut a barbed suture in a simple manner and can accurately adjust the tension of the suture, so that the surgery can be more conveniently and precisely conducted.

In order to achieve the above objects, according to one aspect of the present invention, there is provided a breast shaping method using a barbed suture in breast fat grafting, the method including: after breast fat grafting, inserting a tensioning barbed suture from deep soft tissues (muscle or pericondrium-periostium) into and along a subdermal layer of an existing or new inframammary fold, with an end portion of the barbed suture being left outside of the skin, thereby allowing the barbed suture to be tensioned; tensioning the end portion of the barbed suture arranged by the insertion of the barbed suture, so that the barbed suture pulls tissues of the subdermal layer, thereby lifting and nicely defining an indentation of the inframammary fold; and cutting the end portion of the barbed suture outside of the skin after the tensioning of the barbed suture.

Here, the barbed suture inserting step may include: inserting a first section of the cog thread from the deep soft tissues (the muscle or the pericondrium-periostium) in any one of a medialmost portion and a lateralmost portion of the inframammary fold, with respect to a central portion of the cog thread, to and along the subdermal layer of the inframammary fold, with an end portion of the first section of the cog thread being exposed from the skin; and inserting a second section of the cog thread from the deep soft tissues (the muscle or the pericondrium-periostium) in other one of the medialmost portion and the lateralmost portion of the inframammary fold, with respect to the central portion of the cog thread, to and along the subdermal layer of the inframammary fold, with an end portion of the second section of the cog thread being exposed from the skin.

Furthermore, the barbed suture-tensioning step may include drawing a portion of the cog thread out of the subdermal layer by pulling the end portions of the cog thread exposed out of the skin while pressing the inframammary fold.

In addition, the breast shaping method may further include implanting fat tissues into a breast to increase a volume and improve shape of the breast before the insertion of the barbed suture.

According to another aspect of the present invention, provided is a barbed suture handling device including: a holder gripping and fixing an end portion of a barbed suture;

a body supporting the holder; and a cutter disposed on the body to cut the barbed suture gripped by the holder. The barbed suture may be inserted into a subdermal layer of an inframammary fold, with an end portion of the barbed suture being exposed out of the skin.

In addition, the body may be a hollow extension tube accommodating and allowing the barbed suture to pass therethrough, with the holder being provided on a leading end of the extension tube. The holder may include: a rotational keeper rotatably disposed on an end portion of the extension tube via a support pin, one end portion thereof being located inside of the extension tube, and the other end portion of thereof being located outside of the extension tube; and an elastic support elastically supporting the rotational keeper, with one end portion thereof pressing the barbed suture inserted into the extension tube to prevent the barbed suture from slipping from the extension tube.

Furthermore, the rotational keeper may include a pressing portion on the other end portion, the pressing portion being pressed by a user to detach one end portion of the rotational keeper from the barbed suture.

In addition, the barbed suture handling device may further include a tension sensor provided within the extension tube to detect an amount of tension applied to the barbed suture when the holder pulls the extension tube in a position in which the barbed suture is fixed.

Furthermore, the barbed suture handling device may further include a console box disposed on the extension tube, the console box including an output section connected to the tension sensor to output the amount of tension detected by the tension sensor.

In addition, the output section may include a display outputting the amount of tension detected by the tension sensor. The console box may include an on/off switch to turn the display on and off.

Furthermore, the display may be a touchscreen panel allowing an intended value of tension to be input thereon. The console box may further include a lamp that is lit when the tension sensor detects the amount of tension input via the touchscreen panel.

In addition, the extension tube may include an entrance blade on a leading end to cut the barbed suture inserted into the extension tube. The cutter may include an elastic cutter disposed on one portion of the extension tube to be manipulated by a user to guide the barbed suture toward the entrance blade and cut the barbed suture.

Furthermore, the elastic cutter may include: a fixing portion fixed to one portion of the extension tube; a supporting portion provide integrally with the fixing portion, adjoining the extension tube, and having a curved shape; an operating plate provided integrally with the supporting portion, extending in a longitudinal direction, and spread from the extension tube; and a cutting blade provided integrally with an extension end portion of the operating plate, and bent toward the entrance blade. When the operating plate is pressed in a direction of the extension tube, the cutting blade may intersect the entrance blade to cut the barbed suture.

In addition, the extension tube may have a cutter recess supporting the fixing portion of the elastic cutter, such that the fixing portion is detachably fitted into the cutter recess. The elastic cutter may be formed by bending a band-shaped member having a predetermined thickness and width, and may be fitted into the cutter recess to be supported thereby.

Furthermore, the extension tube may be a pair of extension tubes.

BRIEF DESCRIPTION OF THE DRAWINGS

The above and other objects, features and advantages of the present invention will be more clearly understood from the following detailed description when taken in conjunction with the accompanying drawings, in which:

FIGS. 7A, 7C and 7E are illustrating a scares control on breast footprint and shape when the present invention is not used, compared to FIGS. 7B, 7D and 7F where the breast shape is controlled and enhanced due to the present invention applied.

DETAILED DESCRIPTION OF THE INVENTION

Hereinafter, exemplary embodiments of the present invention will be described in more detail with reference to the accompanying drawings.

A breast shaping method according to the present invention, which will be described later, includes inserting a barbed suture into the subdermal layer of an inframammary fold (i.e. a boundary between a breast, chest and abdomen) and tensioning the barbed suture inserted into the subdermal layer.

When the inserted barbed suture is tensioned, the tissues of the subdermal layer are pulled by the barbed suture, so that the boundary line of the inframammary fold is clearly defined. When the boundary line is clearly defined, breasts are shaped to be high and busty and thus are attractive and beautiful.

The breast shaping method generally includes: inserting a tensioning barbed suture into a subdermal layer of an inframammary fold, with a portion of the barbed suture being left outside of the skin, thereby allowing the barbed suture to be tensioned and the other portion placed within deeper tissue planes (chest muscles/pericondrium-periosteum); tensioning the barbed suture by pulling the portion of the barbed suture left outside of the skin, so that the inframammary fold is slighted lifted and nicely indented; and cutting the portion left outside of the skin after completion of the tensioning.

The barbed suture is a surgical suture widely used in plastic surgery. The type of the barbed suture may be variously changed depending on the condition of the subdermal tissue and the purpose of the surgery. That is, the term "barbed suture" used herein is a concept collectively including, but not limited to, bidirectional or mono-directional cog thread, mono-thread, cutting thread, and molding thread. In addition, the size, physical property, material, or the like of each thread may variously differ as required.

A breast shaping method and a suture handling device according to exemplary embodiments will be described by exemplifying a case in which a bidirectional cog thread, from among the above-mentioned bidirectional and monodirectional cog threads, is handled. In addition, cogs of the bidirectional cog thread are oriented in opposite directions with respect to a central portion of the cog thread.

Figure 1A:
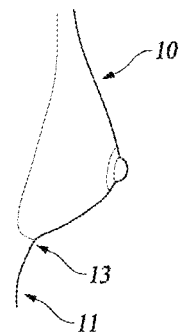
FIGS. 1A to 1D are views illustrating a breast shaping method according to an embodiment of the present invention.
Figure 1B:
Figure 1B:
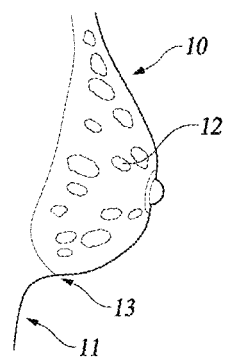
Figure 1D:
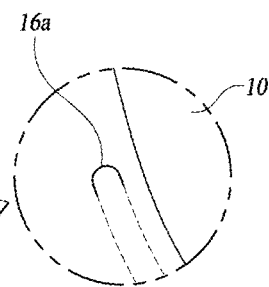
Figure 1D:
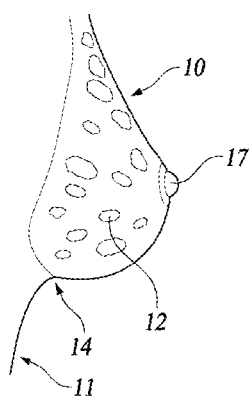
Figure 1C:
Figure 1C:
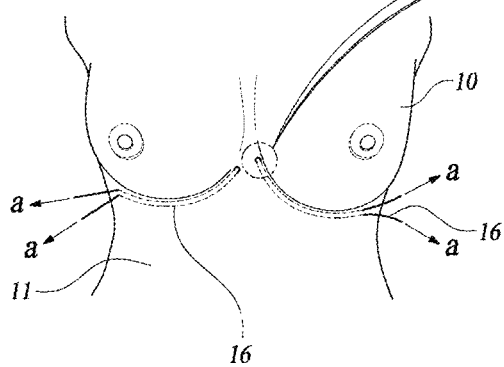
Figure 2:
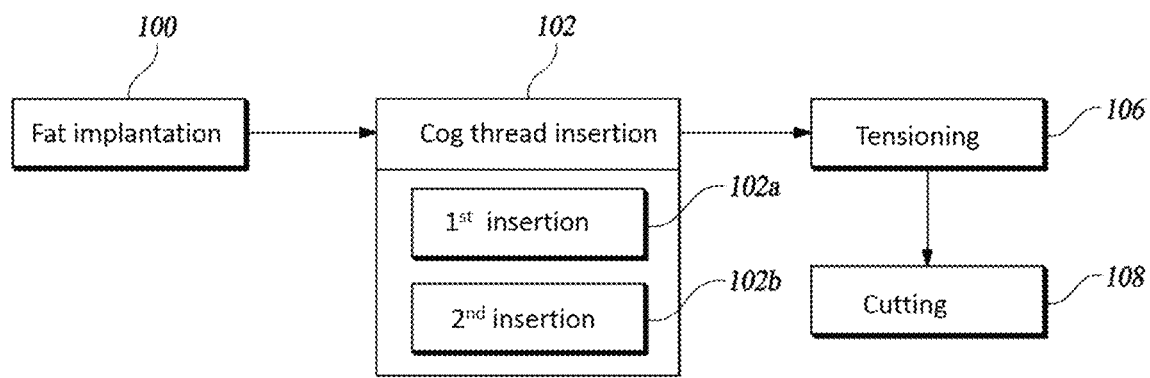
FIG. 2 is a block diagram illustrating the breast shaping method according to an embodiment of the present invention.

FIGS. 1A to 1D are views illustrating a breast shaping method according to an embodiment of the present invention, and FIG. 2 is a block diagram illustrating the breast shaping method according to an embodiment of the present invention.

As illustrated in FIG. 2, the breast shaping method according to the embodiment includes a fat implantation step 100, a cog thread insertion step 102, a tensioning step 106, and a cutting step 108.

The fat implantation step 100 is a step of implanting fat into a breast 10, which is subjected to surgery since the breast is considered to be relatively small/malformed/asymmetric, as illustrated in FIG. 1A. The fat 12 implanted into the breast 10 increases the overall volume of the breast 10. As schematically illustrated in FIG. 1B, the volume of the breast 10 into which the fat 12 is implanted is greater than the volume of the non-implanted breast illustrated in FIG. 1A. The fat implantation is conducted by a typical fat implantation method.

The implantation of fat cause soft tissue edema, thereby swelling the breasts. At the end of fat graft procedure, the shaping surgery is conducted. However, when the volume of the breasts is determined to be sufficient already, the fat implantation step 100 may be omitted. In FIGS. 1A to 1D, reference numeral 13 indicates the inframammary fold. The inframammary fold refers to a line below the breast, i.e. the boundary line between the breast 10 and the upper abdomen 11. The inframammary fold is a body portion into which a cog thread 16 is to be implanted and in which the implanted cog thread 16 is to be tensioned.

The subsequent cog thread insertion step 102 is a process of inserting the tensioning bidirectional cog thread 16 into the subdermal layer of the inframammary fold 13. In particular, as illustrated in FIG. 1C, both end portions of the cog thread 16 must be exposed from the skin. The use of thread allow to control the position and shape of existing or new inframammary fold by slight lift and creating a nice indentation; moreover the breast footprint (i.e. breast width is controlled); finally the placed threads allow a favourable redirection of postoperative interstitial pressure (edema) toward the lower pole favouring a lower pole convexity thus further improving breast shape.

The cog thread insertion step 102 includes a first insertion procedure 102a and a second insertion procedure 102b.

At the beginning of surgery (before fat grafting and before thread placement, the inframammary fold is marked with methylene blue. The first insertion procedure 102a is a procedure of inserting about one half of the cog thread 16, with respect to a central portion 16a of the cog thread 16, first into muscle/pericondrium-periostium of any one of the medialmost and lateralmost portion of the inframammary fold, and then into the subdermal layer along the desired inframammary fold, with an end portion of the half being left outside of the skin to be exposed externally. This insertion is made with a curved sharp eye needle similar to Deshamps needle which is then removed.

Then, one end portion of the cog thread is passed through an eye of a surgical needle (not shown) and this needle is completely passed through the subdermal layer. Since the cog thread is hooked by the eye of the needle, while the needle passes through the subdermal layer, the cog thread is pulled by the needle so as to extend within the subdermal layer. When the needle has completely passed through the subdermal layer of the inframammary fold, the cog thread exits the skin while being hooked by the eye of the needle. Accordingly, the end portion of the cog thread hooked by the eye of the needle is exposed from the skin, with the remaining portion of the cog thread being placed within the subdermal layer.

After the needle has completely passed through the subdermal layer, and then the cog thread is removed from the eye of the needle. Subsequently, the second insertion procedure 102b is followed.

The second insertion procedure 102b is a process of inserting the other half of the cog thread 16, with respect to the central portion 16a of the cog thread 16, first into muscle/pericondrium-periostium of the remained one of the medialmost and lateralmost portion of the inframammary fold, and then into the subdermal layer along the desired inframammary fold, with an end portion of the other half being left outside of the skin to be exposed externally.

FIG. 1C illustrates the shape of the breasts after the first and second insertion procedures 102a and 102b are finished. As illustrated in FIG. 1C, the cog threads 16 are buried in the inframammary folds 13 of both breasts 10. In particular, the central portion 16a and both end portions of each of the cog threads 16 are exposed from the skin.

The subsequent tensioning step 106 is a process of pulling both end portions of each of the cog threads 16 in directions indicated by arrows a. Here, both end portions of each of the cog threads 16 may be tensioned simultaneously or sequentially one by one. In particular, when the cog thread is tensioned, the surrounding portions of the hole, through which the cog thread is pulled from the skin, must be pressed.

When the cog threads 16 are pulled in the directions indicated by the arrows a, cogs of the cog threads 16 inserted into the subdermal layer penetrate into the subdermal tissues and pull the subdermal tissues, thereby lifting the inframammary folds 13 and the surroundings of the inframammary folds 13. The inframammary folds 13 and the surroundings thereof are tightened by the cog threads, clear boundary lines 14 are shaped, as illustrated in FIG. 1D.

Referring to FIG. 1D, the breast 17 has the shape of a drop of water, with the upper portion being generally flat and slightly concave, and the lower portion being convex. For reference, the breast having the tear-drop shape is fashionable among young women.

When an intended level of lifting is performed by properly tensioning both end portions of the cog thread 16, the cutting step 108 is performed. The cutting step 108 is a process of cutting the portions of the cog thread left outside of the skin, so that the cog thread is not visually recognized. The portions of the cog thread left in the subdermal layer after the cutting step 108 gradually dissolve over time.

Figure 7A:
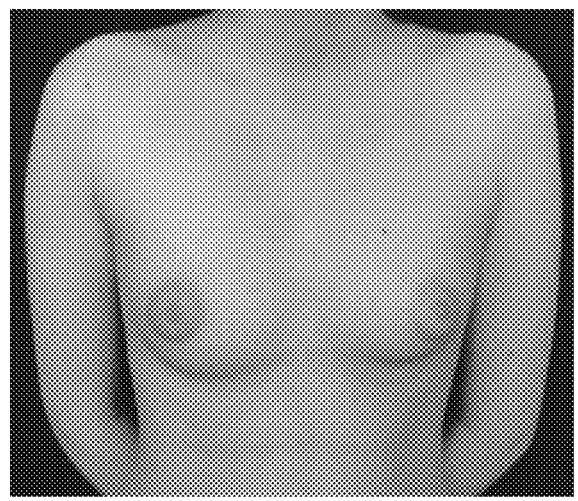
FIGS. 7A to 7F are images referring to the present invention, where
Figure 7B:
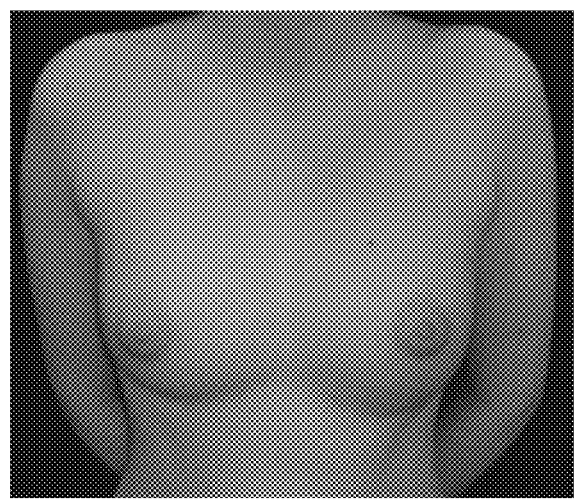

FIGS. 7A and 7B are images illustrating shapes of breasts before and after a surgery conducted by a related-art breast shaping method, while FIGS. 7C to 7F are images illustrating shapes of breasts before and after a surgery conducted by the breast shaping method according to an embodiment of the present invention, compared with the breasts conducted by the related-art breast shaping method.

Referring to FIGS. 7A and 7B, it can be appreciated that, in the breasts produced without using the present invention, the inframammary folds were still unclear and the right and left breasts were more asymmetrical. As illustrated in FIG. 7B, the right breast was more sagged than the left breast.

Figure 7C:
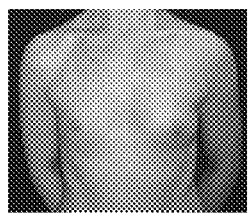
Figure 7D:
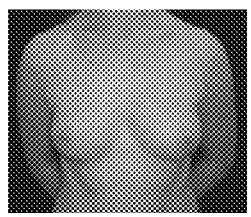
Figure 7E:
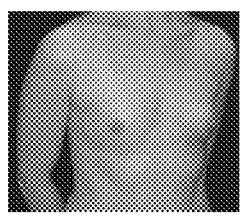
Figure 7F:
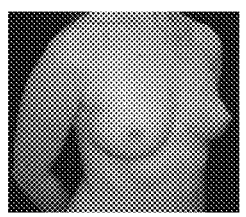

In contrast, it can be appreciated that, in the breasts produced by the breast shaping method according to an embodiment of the present invention, the inframammary folds were changed to be remarkably clear, as illustrated in FIGS. 7D and 7F. Specifically, before the surgery, the breasts were generally flat and the inframammary folds were unclear, as illustrated in FIGS. 7C and 7E. After the surgery, the breasts were reshaped to be higher, better projection and defined shaped including the inframammary folds were clear. In addition, a cog thread handling device is necessary as a tool for performing the shaping method. The cog thread handling device 20 according to the present invention includes a thread holder gripping and holding one end of a cog thread; a body supporting the thread holder; and a cutter mounted on the body to cut the cog thread gripped by the thread holder.

Figure 3:
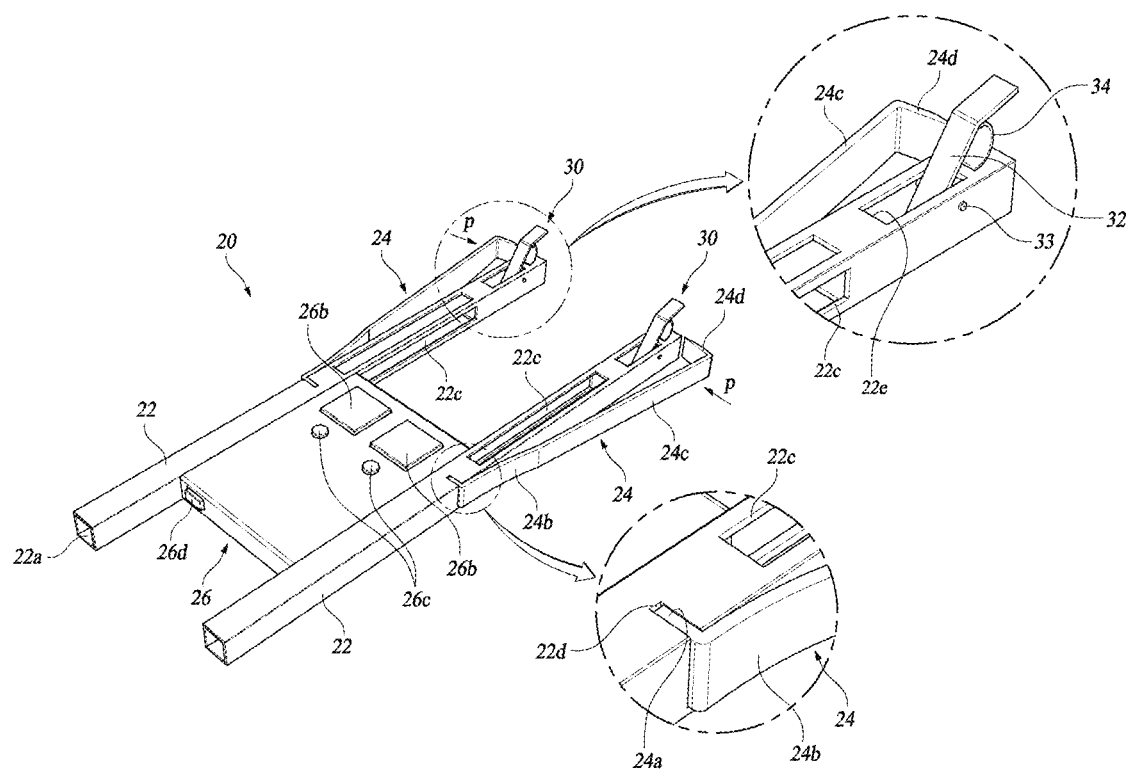
FIG. 3 is a perspective view illustrating a cog thread handling device according to an embodiment of the present invention.

FIG. 3 is a perspective view illustrating a cog thread handling device 20 according to an embodiment of the present invention. The cog thread handling device 20 is a device holding and pulling the cog thread 16 in the direction indicated by an arrow a in FIG. 1C, and cutting the cog thread 16 when the cog thread 16 is properly tensioned.

As illustrated in FIG. 3, the cog thread handling device 20 according to the present embodiment includes a pair of extension tubes 22, a console box 26, a thread holder 30, and an elastic cutter 24.

First, each of the extension tubes 22 has the shape of a hollow tube. As illustrated in FIG. 6B, the extension tube 22 accommodates and allows the cog thread 16 to pass therethrough. The extension tube 22 is a body portion supporting the thread holder 30, which will be described later.

The extension tube 22 has a rectangular cross-sectional shape, linearly extends, and has a plurality of side slots 22*c* in side portions. The side slots 22*c* are holes through which an inner passage 22*a* of the extension tube 22 is open sideward. The cog thread 16 introduced into the extension tube 22 may protrude out of the extension tube 22 through the side slots 22*c*. When the length of the cog thread 16 is sufficiently long, the cog thread 16 may reach to the rear side of the extension tube by completely passing through the passage 22*a*. In addition, an entrance blade 22*b* (see FIG. 5) is provided on the leading end of the extension tube 22.

The extension tubes 22 are provided on both sides of the console box 26 to be spaced apart from each other. Since the two extension tubes 22 are applied, it is possible to simultaneously tension or cut both ends of the cog thread 16. The distance between and size of the extension tubes 22 may be varied as required.

Figure 5:
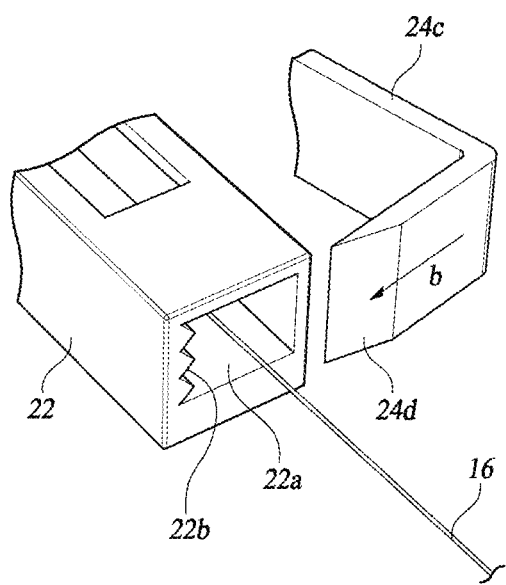
FIG. 5 is a perspective view illustrating leading end portions of the extension tube and the elastic cutter illustrated in FIGS. 3 and 4.

FIG. 5 is a perspective view illustrating leading end portions of the extension tube 22 and the elastic cutter 24.

As illustrated in FIG. 5, a toothed entrance blade 22*b* is provided in the leading end portion of the extension tube 22. The toothed entrance blade 22*b* cuts the cog thread 16 (inserted in the passage 22*a*) by working in concert with a cutting blade 24*d*, which will be described later. The cutting blade 24*d* moves in a direction indicated by an arrow b to cut the cog thread 16 by working in concert with the entrance blade 22*b*. Although the entrance blade 22*b* is illustrated as being toothed in FIG. 5, the shape of the entrance blade 22*b* may be variously changed as long as the entrance blade 22*b* cut the cog thread 16.

Figure 6A:
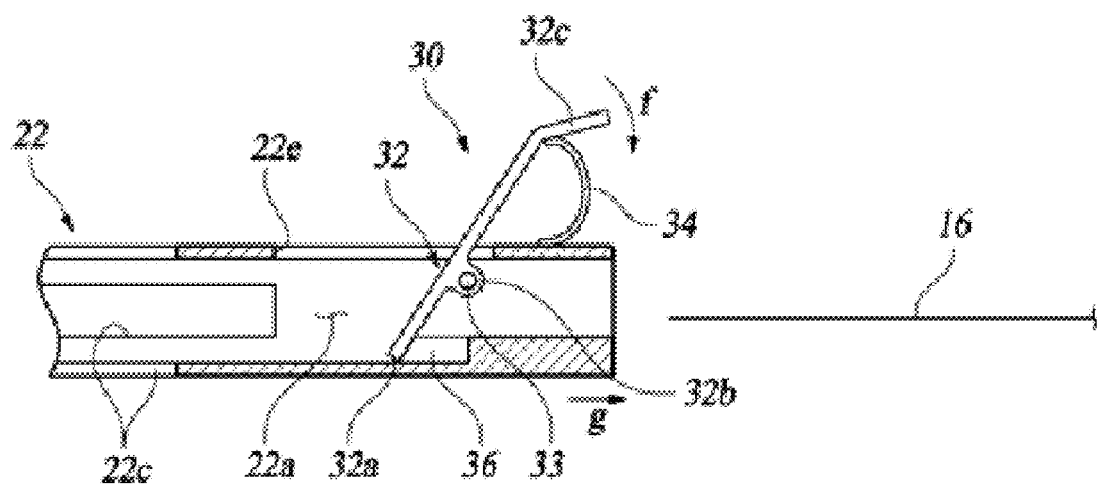
FIGS. 6A to 6D are fragmentary cross-sectional views illustrating the operation of the cog thread handling device according to an embodiment of the present invention.
Figure 6B:
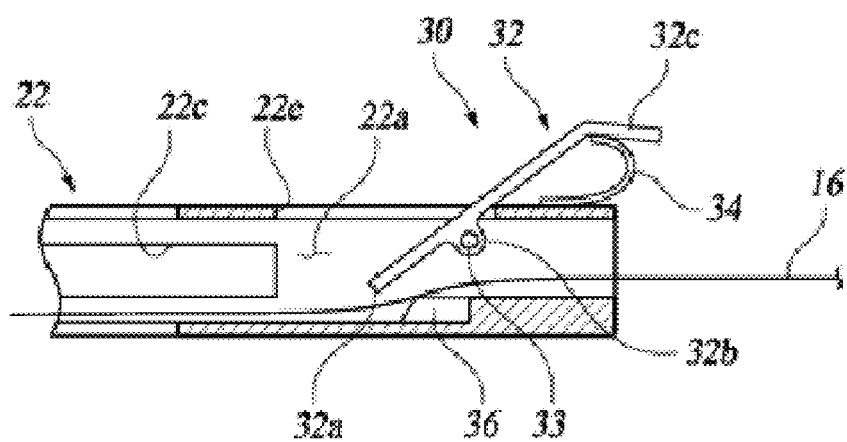
Figure 6C:
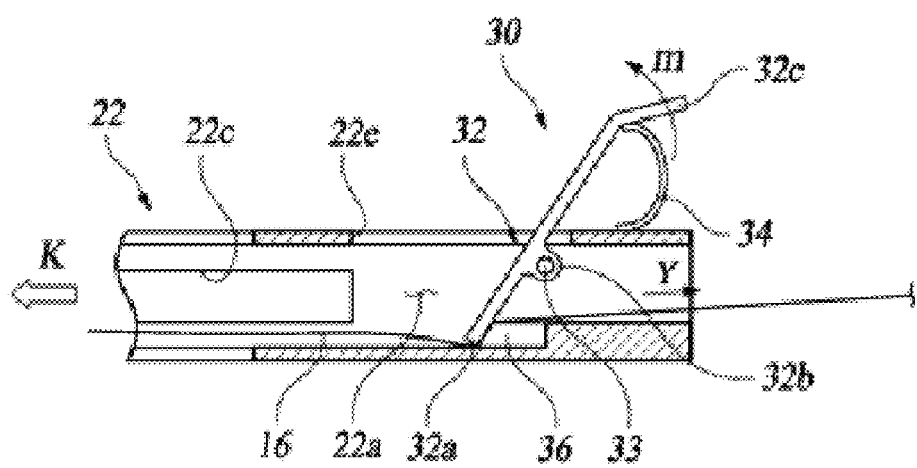
Figure 6D:
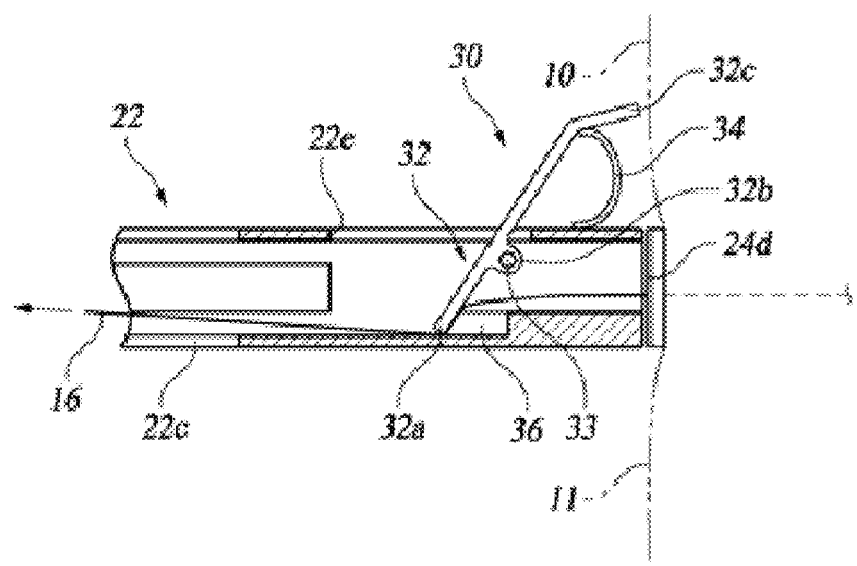

As illustrated in FIG. 6C, the thread holder 30 presses the cog thread 16 that has entered the extension tubes 22 to prevent the cog thread 16 from leaving the passage 22*a*. The thread holder 30 includes a rotational keeper 32 and an elastic support.

The rotational keeper 32 is maintains a mounted position by means of a support pin 33 while extending through a lever hole 22*e*. The rotational keeper 32 is a band-shaped member having a predetermined width and thickness, and has a hinge 32*b* into which the support pin 33 is fitted.

The support pin 33 extends through the hinge 32*b*, with both ends thereof being fixed to the extension tube 22. The rotational keeper 32 may rotate about the support pin 33 acting as the center of rotation, in a direction indicated by an arrow f illustrated in FIG. 6A or in an opposite direction indicated by an arrow m illustrated in FIG. 6C.

In addition, one end portion, i.e. a lower end portion accommodated in the passage 22*a*, of the rotational keeper 32, is a thread pressing portion 32*a* that actually presses the cog thread. The thread pressing portion 32*a* serves to press the cog thread that has entered the inside of the extension tube 22, thereby preventing the cog thread from slipping in a direction indicated by an arrow y. Force with which the thread pressing portion 32*a* presses the cog thread 16 is transferred from an elastic support, i.e. a leaf spring 34.

A pressing portion 32*c* is located on the other end portion of the rotational keeper 32. The pressing portion 32*c* is a portion that a user presses with a finger. When the pressing portion 32*c* is pressed in the direction indicated by the arrow f, the thread pressing portion 32*a* is detached from the cog thread 16, so that the cog thread 16 can be slipped in the direction indicated by the arrow y, as illustrated in FIG. 6C.

In addition, the leaf spring 34 is provided below the pressing portion 32*c*. The leaf spring 34 is a band-shaped member having a predetermined level of elasticity. In an elastically defamed state, one end of the leaf spring 34 is fixed to the pressing portion 32*c* while the other end of the leaf spring 34 is fixed to the extension tube 22. The leaf spring 34 elastically supports the pressing portion 32*c* in the direction indicated by the arrow m.

In addition, a tension sensor 36 is disposed inside of the extension tubes 22. The tension sensor 36 serves to detect tension applied to the cog thread 16 and transfer the detected tension to the console box 26, which will be described later. In this regard, the tension sensor 36 is connected to the console body in a wired or wireless means. The tension sensor 36 will be described later.

The elastic cutter 24 is intended to cut the cog thread 16 gripped and tensioned in the extension tube 22, and includes a fixing portion 24*a*, a supporting portion 24*b*, an operating plate 24*c*, and the cutting blade 24*d*. The elastic cutter 24 is elastically deformable. For example, it is possible to push and move the cutting blade 24*d* in a direction indicated by an arrow p, as illustrated in FIG. 3. When the pushing force is removed, the cutting blade 24*d* can be elastically returned to the initial position.

The elastic cutter 24 is fabricated by machining an elastic metal piece having a predetermined width. The elastic cutter 24 is detachably connected to each of the extension tubes 22. When the elastic cutter 24 is dull, the elastic cutter 24 may be replaced with a new elastic cutter.

In addition, each of the extension tubes 22 is provided with a cutter recess 22*d*, into which the elastic cutter 24 can be detachably fitted. The cutter recess 22*d* is a slit-shaped recess having a predetermined gap, and is open upward and sideward to accommodate and support the fixing portion 24*a*.

The supporting portion 24*b* is a portion integrated with and substantially perpendicularly bent from the fixing portion 24*a*. The supporting portion 24*b* is curved such that the supporting portion 24*b* is spaced farther away from the extension tube 22 in the direction of the leading end thereof. Since the supporting portion 24*b* is curved, the supporting portion 24b functions as a leaf spring. That is, the supporting portion 24b functions as a leaf spring held in the cutter recess 22d.

The operating plate 24c is a portion integrated with and linearly extending from the supporting portion 24b. The user presses the operating plate 24c with a finger so that the cutting blade 24d slides in front of the entrance blade 22b.

The cutting blade 24d is bent with respect to one end of the operating plate 24c, and is provided with a blade edge on the leading end. As the operating plate 24c is pressed in the direction indicated by the arrow p, the cutting blade 24d touches the entrance blade 22b while sliding with respect to the end surface of the extension tube 22. Then, the cog thread 16, accommodated in the passage 22a, is cut by the entrance blade 22b and the cutting blade 24d, as if being cut by scissors.

In addition, the console box 26 remains situated between both extension tubes 22, thereby maintaining the distance between the extension tubes 22. The console box 26 is provided with two touchscreen panels 26b, lamps 26c, an on/off switch 26d, and a battery (not shown).

The console box 26 is connected to the tension sensor 36, and displays measurements of the tension sensors on the touchscreen panels 26b. The touchscreen panels are output sections outputting values of tension detected by the tension sensors. Each of the touchscreen panels is allocated to a corresponding one of the extension tubes 22. Since the two extension tubes 22 are provided, the touchscreen panels 26b are also two.

The touchscreen panels 26b may be used to input information, as well as outputting information. For example, a preferable amount of tension set as required may be input. Here, the preferable amount of tension is determined such that it is not preferable to tension the cog thread with force the same as or greater than the preferable amount of tension. The touchscreen panels 26b allow a maximum amount of force, with which the cog thread 16 is pulled in the direction indicated by the arrow a, to be set.

In addition, the lamps 26c are located on sides of the touchscreen panels 26b, respectively. Each of the lamps 26c is lit when an amount of tension detected by the tension sensor 36 reaches a predetermined amount of tension. The user can adjust the tension on the basis of whether or not the lamps 26c are lit. Although the present embodiment is configured such that the amount of tension is visually recognizable using the lamps 26c, a sound-generating means may be used in place of the lamps.

The on/off switch 26d is a switch with which the console box 26 is turned on and off. As described above, a power supply is provided inside of the console box 26, and serves to determine the supply of power from the power supply.

Figure 4:
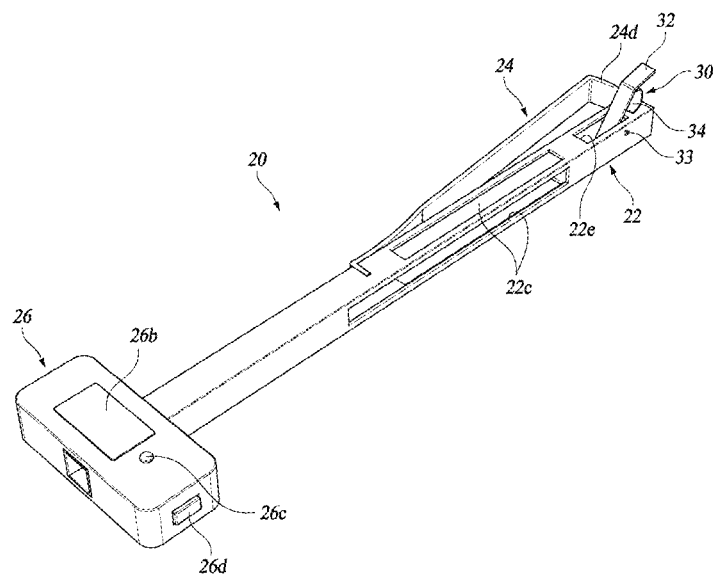
FIG. 4 is a perspective view illustrating a cog thread handling device according to another embodiment of the present invention.

FIG. 4 is a perspective view illustrating a cog thread handling device according to another embodiment of the present invention.

In the following, the same reference numerals will be used to designate to components the same as or similar to those of the foregoing embodiment.

The cog thread handling device 20 illustrated in FIG. 4 includes a single extension tube 22 and a single console box 26. Although the two extension tubes 22 are provided to tension and cut the two cog threads 16 at one time in the embodiment illustrated in FIG. 3, one cog thread is tensioned and cut at one time in the embodiment illustrated in FIG. 4.

In addition, the console box 26 is located on the rear end portion of the extension tube 22. The functions or roles of respective components of the console box 26 are the same as those illustrated in FIG. 3. In particular, in the embodiment illustrated in FIG. 4, the console box 26 is fixed to the rear end portion of the extension tube 22, and the entirety of the console box can be used as a knob.

FIGS. 6A to 6D are fragmentary cross-sectional views illustrating the operation of the cog thread handling device according to an embodiment of the present invention.

FIGS. 6A and 6B illustrate positions in which the extension tube 22 is moved in the direction indicated by the arrow g and the cog thread 16 is inserted into the passage 22a. As illustrated in FIG. 1C, one end portion of the cog thread 16 is inserted into the extension tube 22 by holding the cog thread 16, exposed out of the skin, with one hand and moving the extension tube 22 with the other hand.

Here, the thread pressing portion 32a must be detached from the bottom by pressing the pressing portion 32c with a finger in the direction indicated by the arrow f. That is, the passage 22a must be opened by pivoting the thread pressing portion 32a in the direction indicated by the arrow f so that the cog thread 16 enters the passage 22a.

When the cog thread 16, inserted into the passage 22a by the above-described process, is long enough, one end portion of the cog thread 16 can completely pass through the extension tube 22 and protrude from the rear end of the extension tube 22. However, when the cog thread is not long enough, one end portion of the cog thread 16 is exposed out of the extension tube 22 through the side slots 22c.

When the leading end portion of the extension tube 22, moving in the direction indicated by the arrow g while accommodating the cog thread 16, finally reaches the inframammary fold 13, the force with which the pressing portion 32c is pressed is removed. When the pressing portion 32c is released, the pressing portion 32c moves upwards in the direction indicated by the arrow m, in response to the action of the leaf spring 34, and the thread pressing portion 32a fixes the cog thread 16 between the thread pressing portion 32a and the tension sensor 36. Then, the cog thread 16 is gripped and fixed between the thread pressing portion 32a and the tension sensor 36.

When the cog thread 16 is fixed to the thread holder 30, the extension tube 22 is pulled in the direction indicated by an arrow k, as illustrated in FIG. 6C, while the inframammary fold 13 is pressed with one hand. When the cog thread 16 is tensioned in response to the extension tube 22 being pulled, one portion of the cog thread 16 slips out of the subdermal layer, and the other portion of the cog thread 16 penetrates and locks into the inner tissues of the subdermal layer. At the same time, the other portion of the cog thread 16 lifts the inframammary fold 13 while pulling the subdermal tissues. As described above, the inframammary fold 13 is tightened by the cog thread, thereby shaping the boundary line 14.

Here, the tension applied in the direction indicated by the arrow k is detected by the tension sensor 36 in real time. The tension sensor 36 transfers detected information to the console box 26. When the amount of tension of the cog thread 16, during pulling of the extension tube 22 in the direction indicated by the arrow k, is greater than a preset amount of tension, the lamp 26c provided in the console box is lit, thereby notifying that the amount of tension of the cog thread 16 is greater than the preset amount of tension.

When pulling of the cog thread 16 is completed through the above-described process, in a position in which the cog thread 16 is held with one hand to be tensioned, the extension tube 22 is moved toward the inframammary fold 13 to be in close contact with the inframammary fold.

Subsequently, the cog thread 16 is cut by manipulating the elastic cutter 24. In this manner, the shaping operation is completed.

The breast shaping method using a barbed suture according to the present invention can provide a breast shape having a clear contour while being high and elastic by tightening the inframammary folds between the breasts and the upper abdomen so as to be more clearly defined. The inframammary fold can be represented by the existing one or, in case of higher native inframammary fold, a new inframammary fold can be designed by the surgeon and the barbed thread used to define the new inframammary fold. Being the thread placed from medialmost and lateralmost end of the inframammary fold, the barbed thread not only highly defined the intended inframammary fold but it allows to control breast footprint as well (i.e. breast width). When combined with breast fat grafting, the thread allows to immediately define breast boundaries (inframammary fold and breast footprint) but it also allows to control postoperative edema, promoting a favourable interstitial pressure redirection toward the inferior pole thus enhancing the lower pole convexity. In addition, the breast shaping method can reduce the burden of a surgery, being scarless (i.e. millimetric scars), and significantly reduce a recovery time due to any skin dissection. In particular, after the surgery, the effect of the surgery is immediate and, in case of breast fat grafting, further improves by postoperative edema resolution.

In addition, the barbed suture handling device according to the present invention can tension and cut a barbed suture in a simple manner and can accurately adjust the tension of the barbed suture, so that the surgery can be more conveniently and precisely conducted.

Although the exemplary embodiments of the present invention have been described for illustrative purposes, those skilled in the art will appreciate that various modifications, additions and substitutions are possible, without departing from the scope and spirit of the present invention as disclosed in the accompanying claims.

What is claimed is:

1. A breast shaping method using a barbed suture in breast fat grafting, the method comprising:

after breast fat grafting, inserting a tensioning barbed suture from muscle or pericondrium-periostium located beneath any one of a medialmost or a lateralmost portion of an inframammary fold into and along a subdermal layer of the inframammary fold, with an end portion of the barbed suture being left outside of the skin, thereby allowing the barbed suture to be tensioned;

tensioning the end portion of the barbed suture arranged by the insertion of the barbed suture, so that the barbed suture pulls tissues of the subdermal layer, thereby lifting and defining an indentation of the inframammary fold; and cutting the end portion of the barbed suture outside of the skin after the tensioning of the barbed suture.

2. The breast shaping method according to claim 1, wherein the insertion of the barbed suture comprises:

inserting a first section of a cog thread from the muscle or the pericondrium-periostium in any one of a medialmost portion and a lateralmost portion of the inframammary fold, with respect to a central portion of the cog thread, to and along the subdermal layer of the inframammary fold, with an end portion of the first section of the cog thread being exposed from the skin; and inserting a second section of the cog thread from the muscle or the pericondrium-periostium in other one of the medialmost portion and the lateralmost portion of the inframammary fold, with respect to the central portion of the cog thread, to and along the subdermal layer of the inframammary fold, with an end portion of the second section of the cog thread being exposed from the skin.

3. The breast shaping method according to claim 2, wherein the tensioning of the barbed suture comprises drawing a portion of the cog thread out of the subdermal layer by pulling the end portions of the cog thread exposed out of the skin while pressing the inframammary fold.

4. The breast shaping method according to claim 1, further comprising implanting fat tissues into a breast to increase a volume and improve shape of the breast before the insertion of the barbed suture.

* * * * *